(12) United States Patent
Slater et al.

(10) Patent No.: US 11,592,398 B2
(45) Date of Patent: Feb. 28, 2023

(54) AUGMENTED RAMAN ANALYSIS OF A GAS MIXTURE

(71) Applicant: Kaiser Optical Systems Inc., Ann Arbor, MI (US)

(72) Inventors: Joseph B. Slater, Dexter, MI (US); James M. Tedesco, Livonia, MI (US); Francis Esmonde-White, Ann Arbor, MI (US)

(73) Assignee: Endress+Hauser Optical Analysis, Inc., Ann Arbor, MI (US)

( * ) Notice: Subject to any disclaimer, the term of this patent is extended or adjusted under 35 U.S.C. 154(b) by 443 days.

(21) Appl. No.: 16/984,748

(22) Filed: Aug. 4, 2020

(65) Prior Publication Data

US 2020/0363339 A1 Nov. 19, 2020

Related U.S. Application Data

(62) Division of application No. 15/830,094, filed on Dec. 4, 2017, now Pat. No. 10,768,115.

(51) Int. Cl.

| *G01J 3/44* | (2006.01) |
|---|---|
| *G01N 21/65* | (2006.01) |
| *G01N 21/35* | (2014.01) |
| *G01N 33/00* | (2006.01) |
| *G01N 21/3504* | (2014.01) |
| *G01N 21/359* | (2014.01) |

(52) U.S. Cl.
CPC ............. *G01N 21/65* (2013.01); *G01N 21/35* (2013.01); *G01N 21/3504* (2013.01); *G01N 33/0004* (2013.01); *G01N 21/359* (2013.01)

(58) Field of Classification Search
CPC ........ G01N 21/65; G01N 21/35; G01N 21/31; G01N 21/3504; G01N 33/0004; G01N 21/359; G01J 3/44; G01J 3/02; A61B 5/0075
See application file for complete search history.

(56) References Cited

U.S. PATENT DOCUMENTS

| 5,822,058 | A | 10/1998 | Adler-Golden et al. | |
|---|---|---|---|---|
| 6,941,230 | B1 * | 9/2005 | Stirnberg | G01J 3/32 702/30 |
| 2002/0040590 | A1 * | 4/2002 | Schley | G01N 21/3504 356/437 |
| 2012/0004861 | A1 | 1/2012 | Cline et al. | |

FOREIGN PATENT DOCUMENTS

| CN | 102539377 A | 7/2012 |
|---|---|---|
| CN | 105806825 A | 7/2016 |
| EP | 0947825 A1 | 10/1999 |

* cited by examiner

*Primary Examiner* — Abdullahi Nur
(74) *Attorney, Agent, or Firm* — Mark A. Logan; Endress+Hauser (USA) Holding, Inc.

(57) ABSTRACT

The present disclosure includes discloses a method for analyzing a multi-component gas sample using spectroscopy in combination with the measurement of extrinsic or intrinsic properties of the gas sample. The results of the spectroscopic analysis and the measurement are combined to quantify a gas component unseen by the spectroscopic analysis.

6 Claims, 3 Drawing Sheets

AUGMENTED RAMAN ANALYSIS OF A GAS MIXTURE

CROSS-REFERENCE TO RELATED APPLICATION

The present application is a divisional application of U.S. patent application Ser. No. 15/830,094, filed on Dec. 4, 2017, the entire contents of which are incorporated herein by reference.

TECHNICAL FIELD

The present disclosure relates generally to analyzing gas mixtures using Raman spectroscopy.

BACKGROUND OF THE INVENTION

Composition analysis of a gas sample by Raman spectroscopy allows the measurement of the abundance of the chemical species within the gas sample for those chemical species composed of at least two atoms. Species composed of just one atom, such as the noble gases helium and argon, and ionic-bonded substances like salts, are invisible to Raman spectroscopy. In practice, such Raman-invisible species are present in some chemical mixtures and often need to be quantified.

Absorption spectroscopy such as near infrared spectroscopy and infrared spectroscopy suffer similar limitations as the Raman analysis. That is, substances such as homonuclear diatomics ($O_2$, $N_2$, etc.) and ionic-bonded salts are invisible to the absorption spectroscopy, but nevertheless these substances are present in some chemical mixtures and often need to be quantified.

In sample streams containing a component invisible to Raman or absorption spectroscopy, it is often necessary to supplement the spectroscopy measurements to quantify invisible species and obtain full composition analysis. For example, in the synthesis loop in a fertilizer plant argon is present along with other gases. Though Raman spectroscopy can characterize most of the gases in a sample, the detection of argon requires another technology such as gas chromatography or mass spectrometry. These methods are relatively expensive and not well suited to in situ detection within a pipeline or a reactor.

Less costly analysis methods exist which can quantify the Raman-invisible species, but such methods work well for mixtures with only a few components, ideally mixtures containing only two gases, i.e., binary mixtures. But in many industrial applications many gases will be present in a sample, and a direct application of methods for solving binary mixtures must be modified, and assumptions must be made regarding which components are changing and which are stable. Accordingly, there remains a need for further contributions in this area of technology to enable compositional analysis of mixtures that include spectroscopic-invisible species.

SUMMARY OF THE INVENTION

The present disclosure discloses a method for analyzing the composition of a multi-component matter sample including determining a first composition of a multi-component matter sample using a spectroscopic device; calculating a relative composition matrix containing a normalized molar amount of each component of the matter sample, based on the first composition; calculating a value of a first secondary property of the matter sample using the relative composition matrix; measuring a value of the first secondary property of the matter sample with a sensor embodied to measure the value of the first secondary property; and determining whether a first difference between the calculated value of the first secondary property and the measured value of the first secondary property exceeds a first threshold, wherein upon determining that the first difference exceeds the first threshold: attributing the first difference to a component invisible to the spectroscopic device; calculating a first amount of the spectroscopic-invisible component using the first difference; adding the first amount of the spectroscopic-invisible component to the relative composition matrix; and adjusting the normalized molar amount of each component in the relative composition matrix to account for the first amount of the spectroscopic-invisible component.

The method may include using a Raman spectroscopic device, and spectroscopic-invisible would be defined as invisible to Raman spectroscopy. Alternately, the method may include using a near infrared absorption spectroscopic device, and spectroscopic-invisible would be defined as invisible to near infrared absorption spectroscopy. Alternately, the method may include using an infrared absorption spectroscopic device, and spectroscopic-invisible would be defined as invisible to infrared absorption spectroscopy.

The method may be employed for matter in a gaseous phase or in a condensed phase.

The first secondary property may be one of the following: thermal conductivity, electrical conductivity, viscosity, pH, density, turbidity, and color-changing chemical reaction.

In an embodiment, the method may include calculating a value of a second secondary property of the matter sample using the relative composition matrix, the second secondary property being different from the first secondary property; measuring a value of the second secondary property of the matter sample with a sensor embodied to measure the value of the second secondary property; and determining whether a second difference between the calculated value of the second secondary property and the measured value of the second secondary property exceeds a second threshold, wherein upon determining that the second difference exceeds the second threshold: attributing the second difference to the spectroscopic-invisible component present in the sample; calculating a second amount of the spectroscopic-invisible component using the second difference; calculating a third amount of the spectroscopic-invisible component using the weighted average of the first amount of the spectroscopic-invisible component and the second amount of the spectroscopic-invisible component; replacing the first amount of the spectroscopic-invisible component in the relative composition matrix with the third amount of the spectroscopic-invisible component; and adjusting the normalized molar amounts of each component in the relative composition matrix to account for the third amount of the spectroscopic-invisible component.

In another embodiment, a method for analyzing the composition of a multi-component gas sample includes: determining a first composition of a multi-component gas sample using a spectroscopic device; calculating a relative composition matrix containing a normalized molar amount of each component of the multi-component gas sample, based on the first composition; calculating an average molar mass of the relative composition matrix using a molar mass and the normalized molar amount of each component of the relative composition matrix; measuring a temperature, a pressure, and a density of the gas sample and calculating an inverse compressibility factor of the gas sample therefrom; calculating a molar amount of a spectroscopic-invisible gas using the average molar mass, the inverse compressibility factor, and a molar mass of the spectroscopic-invisible gas; adding the molar amount of the spectroscopic-invisible gas to the relative composition matrix; and adjusting the normalized molar amount of each component in the relative composition matrix to account for the molar amount of the spectroscopic-invisible gas.

The method may include using a Raman spectroscopic device, and spectroscopic-invisible would be defined as invisible to Raman spectroscopy. Alternately, the method may include using a near infrared absorption spectroscopic device, and spectroscopic-invisible would be defined as invisible to near infrared absorption spectroscopy. Alternately, the method may include using an infrared absorption spectroscopic device, and spectroscopic-invisible would be defined as invisible to infrared absorption spectroscopy.

In another embodiment, a method for analyzing the composition of a multi-component gas sample includes determining a first composition of a multi-component gas sample using a spectroscopic device; calculating a relative composition matrix containing a normalized molar amount of each component of the multi-component gas sample, based on the first composition; measuring a temperature, a pressure, and a density of the gas sample and calculating a first compressibility factor of the gas sample therefrom; estimating a molar amount of a spectroscopic-invisible gas; adding the estimated molar amount of the spectroscopic-invisible gas to the relative composition matrix; adjusting the normalized molar amount of the other components in the relative composition matrix to account for the estimated molar amount of the spectroscopic-invisible gas; calculating a second compressibility factor of the gas sample using the relative composition matrix; determining whether a difference between the first compressibility factor and the second compressibility factor exceeds a threshold, wherein upon determining that the difference exceeds the threshold: adjusting the estimated molar amount of the spectroscopic-invisible gas in the relative composition matrix such that the difference between the first compressibility factor and the second compressibility factor is reduced; repeating the adjusting the normalized molar amount of each component in the relative composition matrix, the calculating a second compressibility factor, and the determining whether a difference between the first compressibility factor and the second compressibility factor exceeds a threshold until the difference does not exceed the threshold.

The method may include using a Raman spectroscopic device and spectroscopic-invisible would be defined as invisible to Raman spectroscopy. Alternately the method may include using a near infrared/infrared absorption spectroscopic device and spectroscopic-invisible would be defined as invisible to near infrared/infrared absorption spectroscopy.

BRIEF DESCRIPTION OF THE DRAWINGS

The described embodiments and other features, advantages, and disclosures contained herein, and the matter of attaining them, will become apparent and the present disclosure will be better understood by reference to the following description of various embodiments of the present disclosure taken in conjunction with the accompanying drawings, wherein.

DETAILED DESCRIPTION

Figure 1:
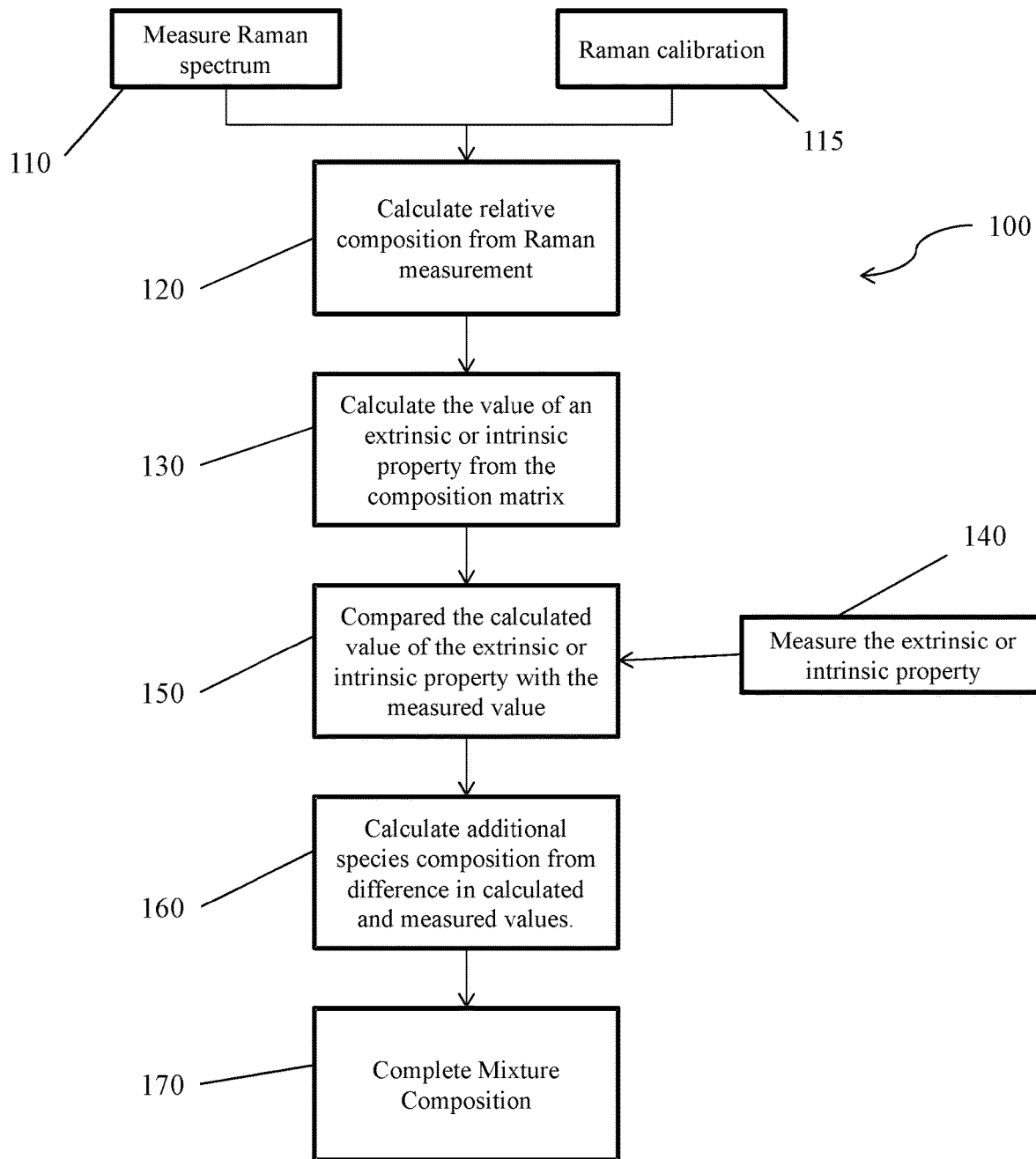
FIG. 1 shows the flow diagram of an embodiment of the disclosed method.

The present disclosure discloses systems and methods for determining the quantities of constituent species of a gas or condensed-phase mixture, including spectroscopic-invisible species. According to at least one aspect of the present disclosure, the methods include supplementing a first analysis of a multi-component sample with a second analysis of that sample. The first analysis may not quantify all of the components in the sample; therefore, a second analysis using tools, detectors, and sensors different from those used in the first analysis is performed, and the results of the two analyses are combined to determine the full composition of the multi-component sample.

For the purposes of promoting an understanding of the principles of the present disclosure, reference will be made to the embodiments illustrated in the drawings, and specific language will be used to describe the same. It will nevertheless be understood that no limitation of the scope of this disclosure is thereby intended.

In at least one embodiment of the present disclosure, the first analysis is performed on a multi-component gas sample using Raman spectroscopy. The first analysis (i.e., the Raman analysis) determines the type and amount of each chemical species present in the gas sample that has a Raman signature. Those substances present that do not have a Raman signature, e.g., substances that do not form molecules or that are ionically bonded, are not detected by Raman spectroscopy because they do not wavelength-shift the light they scatter. Therefore, a second analysis, one which does not use Raman spectroscopy, is performed to measure the presence of the Raman-invisible components.

The second analysis includes the calculation of one or more properties of the gas sample that can also be measured. Accordingly, the second analysis includes the measurement of one or more properties of the gas sample that can also be calculated when the constituents of the gas sample are known. Therefore, the choice of a property of the gas sample to be used in the second analysis, herein referred to as a secondary property, requires that the secondary property can be both calculated and measured.

The term secondary property in this disclosure refers to an extrinsic or intrinsic property of the mixture or of a component of the mixture. Such extrinsic or intrinsic properties include density, thermal conductivity, electrical conductivity, viscosity, turbidity, pH, and color-changing chemical reaction. The primary property of the gas mixture or of a component of the gas mixture as used in this disclosure is the molar amount of the substance.

The disclosed methods are most applicable when it is known, or at least expected, that a particular spectroscopic-invisible component is present in the gas or the condensed-phase mixture. For example, argon gas is often present in the synthesis loop in an ammonia production process. As another example, helium is often present in natural gas extracted from the earth. Knowledge of the type of the spectroscopic-invisible component enables the calculation of the secondary property chosen for the second analysis.

A method 100 according to at least one embodiment of the present disclosure is shown in FIG. 1. The method 100 may be performed on a multi-component gas sample contained in a sample chamber.

The method 100 includes a step 110 of analyzing a multi-component gas sample using a Raman spectrometer device. The Raman spectrometer generates and captures a spectrum of Raman-scattered light.

The method 100 may include a step 115 of retrieving from a database calibration data from a previously performed calibration of the Raman device and adjusting the Raman spectrum using the retrieved calibration data.

The method 100 includes a step 120 of calculating the relative composition of the gas sample from the adjusted Raman spectrum and producing a matrix of the components of the gas sample. The step 120 may include using the calibration data retrieved in step 115 to improve the accuracy of the analysis. The step 120 includes normalizing the components of the matrix by expressing each Raman-detected component as a ratio of the amount of that component to the sum of the amounts of all Raman-detected components. That is, each component is expressed as a percentage of the whole sample. The result of step 120 is a relative composition matrix containing the amounts of each Raman-detected component in the gas sample.

The method 100 includes a step 130 of calculating the value of at least one secondary property of the gas sample using the relative composition matrix as determined in step 120. The secondary property of the gas sample may be an intrinsic property such as thermal conductivity, electrical conductivity, viscosity, and pH, among others. The secondary property of the gas sample may be an extrinsic property such as density and turbidity, among others. The step 130 may include calculating the value of more than one secondary property.

The method 100 includes a step 140 of measuring the value of the secondary property which was calculated in step 130. The measurement of the secondary property (or properties) is performed on the gas sample in the sample chamber using a device embodied to measure that secondary property.

The choice of the secondary property may be partially determined by the availability of a capable measuring device or sensor having sufficient resolution to measure the secondary property of the Raman-invisible component. For example, if the chosen secondary property of the gas sample were thermal conductivity, the resolution of the thermal conductivity measuring device must be greater than the contribution to thermal conductivity that the Raman-invisible gas provides. In certain embodiments, the device or sensor may be capable of measuring more than one secondary property with sufficient accuracy.

The method 100 includes a step 150 of comparing the calculated value of the secondary property with the corresponding measured value of that secondary property. If the calculated value differs from the measured value by at least a threshold value, the difference is attributed to the Raman-invisible gas in the sample. Note the specific value of the threshold will depend on the particular secondary property chosen for the method 100.

The calculated difference in step 150 may be a positive or negative value depending on the choice of the secondary property. With certain secondary properties, it is expected the measured value of that property will be greater than the calculated value if a Raman-invisible component is present in the sample. But with other secondary properties, it might be expected the measured value be less than the calculated value if a Raman-invisible component is present in the sample.

When the difference calculated in step 150 exceeds the threshold value, the method 100 may include a step 160 of calculating the relative amount of the Raman-invisible gas present in the sample. This calculation is performed using the difference between the calculated value and measured value of secondary property.

The method 100 includes a step 170 of adding the amount of the Raman-invisible component that was calculated in step 160 to the relative composition matrix and re-calculating the amounts of the other components that were already in the relative composition matrix. As previously noted, the amount of each component of the gas sample is expressed as a percentage of the whole sample. Therefore, adding the Raman-invisible gas to the relative composition matrix requires the re-calculation of all the components which were already in the relative composition matrix.

In an embodiment of method 100, the method steps may be repeated using a different secondary property of the gas mixture. The amount of the Raman-invisible gas determined in the second iteration can be combined with the amount of the Raman-invisible gas determined in the first iteration for a more accurate final value of the amount of the Raman-invisible gas present in the gas sample. The values from each iteration can be combined through a weighted average, for example. Note the method is not limited to being run only twice on the gas sample, but may be performed several times using different secondary properties each time and re-calculating the relative composition matrix accordingly each time.

The foregoing embodiment of method 100 is not limited to using Raman spectroscopy on a gas sample. In an alternate embodiment of method 100, an absorption spectroscopy (e.g., infrared or near infrared) may be performed on the gas sample. In such an embodiment, the remaining steps of the method are essentially the same. In yet another alternate embodiment of method 100, the substance being analyzed using either Raman or absorption spectroscopy is in the condensed phase. Such analysis of a solid or liquid phase substance may be for determining percent salt content, for example.

Figure 2:
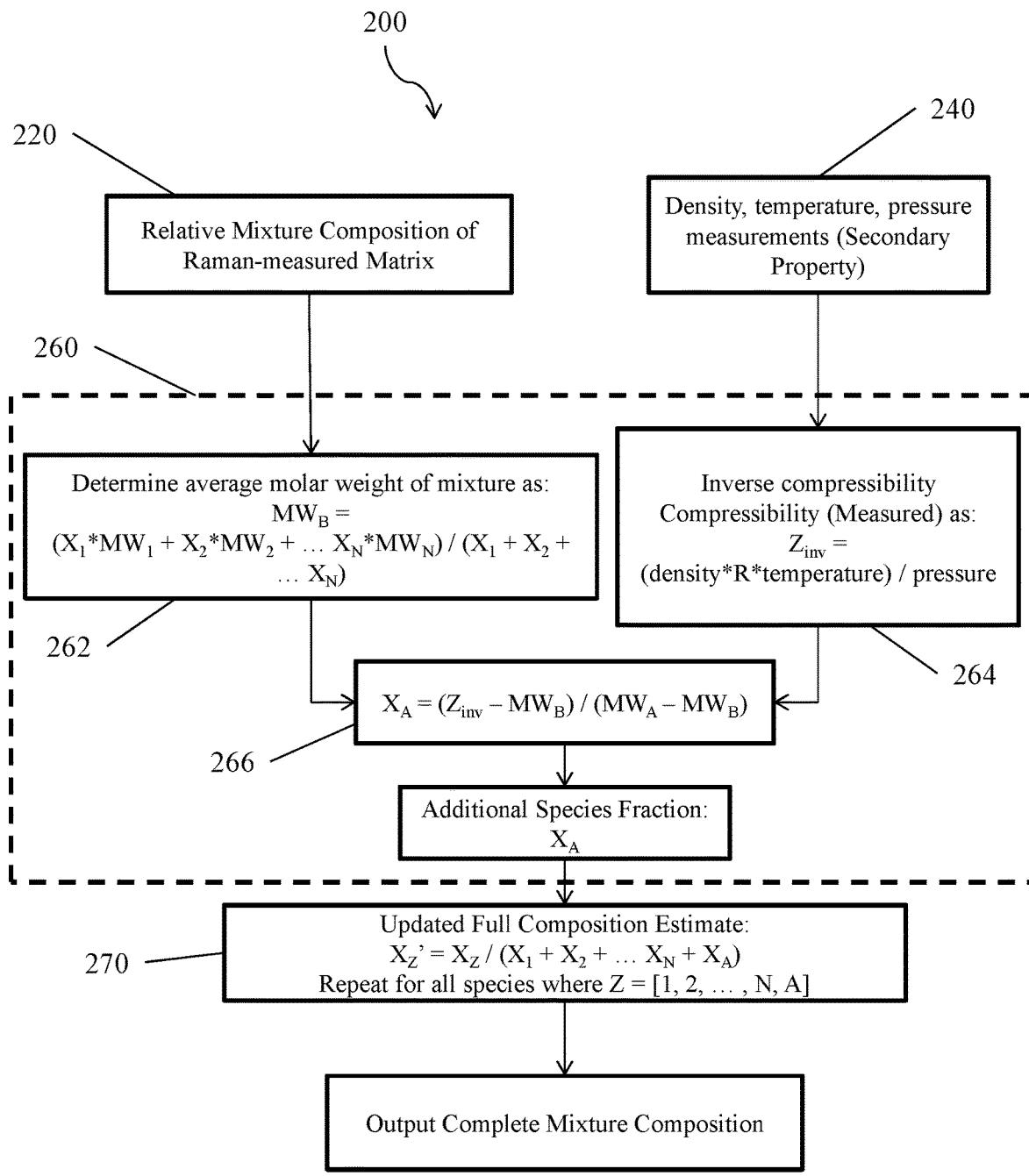
FIG. 2 shows an exemplary calculation of the mixture composition using an ideal gas approximation.

A method 200 according to at least one embodiment of the present disclosure is shown in FIG. 2. The method 200 may be performed on a multi-component gas sample contained in a sample chamber.

The method 200 includes a Raman spectroscopic analysis of the gas sample to generate and to capture a Raman spectrum of the gas sample, which is not shown in FIG. 2.

The method 200 includes a step 220 of calculating the relative composition of the gas sample from the Raman spectrum and producing a matrix of the components of the gas sample. The step 220 includes normalizing the components of the matrix by expressing each Raman-detected component as a ratio of the amount of that component to the sum of the amounts of all Raman-detected components. That is, each component is expressed as a percentage of the whole sample. The result of step 220 is a relative composition matrix containing the amounts of each Raman-detected component in the gas sample.

The method 200 includes a step 240 of measuring one or more secondary properties of the gas mixture. In the embodiment shown in FIG. 2, the density, pressure, and temperature of the gas sample are measured in step 240, but other secondary properties may be measured and used as well.

The method 200 includes a step 260 of calculating the amount of the Raman-invisible gas present using formulae derived from the ideal gas law and using the measured values of one or more secondary properties of the gas. In step 260 the multi-component gas mixture is treated as a simple binary mixture of gases A and B. In this step, gas A of the binary mixture is the Raman-invisible gas. Gas B of the binary mixture is the aggregation of the components determined by the Raman spectroscopy.

To accomplish this simplification and aggregate all the known gases in the gas sample into one representative gas, gas B, a data set of known gases is provided. The substance and amount of each constituent must be accurately determined to enable an accurate calculation of secondary properties of the representative gas. Without the accurate characterization of the gas sample by the Raman spectroscopy, for example, there is no reasonable expectation of accuracy in treating the gas mixture as a binary mixture.

Note though the description of method 200 specifies a Raman spectroscopic analysis of the sample, other spectroscopy methods, such as NIR or IR absorption spectroscopy, may be employed as well. For example, the concentration of homonuclear diatomics such as $O_2$, $N_2$, etc., which are normally invisible to IR absorption spectroscopy, may be determined using the analysis methods of this disclosure.

Step 260 includes a step 262 of calculating the average molar mass of gas B of the binary gas mixture (i.e., $MW_B$ as shown in FIG. 2). In FIG. 2, the molarity of each Raman-detected component is represented by $X_i$. The molar mass of each Raman-detected component is represented by $MW_i$. The number of Raman-detected components is N.

Step 260 includes a step 264 of calculating the inverse of the compressibility factor of the gas sample from the values of the density, temperature, and pressure of the gas sample that were measured in step 240.

Step 260 includes a step 266 in which the molar fraction of gas A (i.e., $X_A$ as shown in FIG. 2), the Raman-invisible gas, is calculated. The inputs to the calculation of the molar fraction of gas A include the inverse compressibility factor calculated in step 264, the average molar mass of gas B calculated in step 262, and the average molar mass of gas A. The average molar mass of gas A is determined by specifying the substance of gas A. That is, the substance of gas A must be known and specified so that an appropriate value of the average molar mass of gas A can be used to calculate the molar fraction of gas A.

The method 200 includes a step 270 of adding the amount of the Raman-invisible component that was calculated in step 266 to the relative composition matrix and re-calculating the amounts of the other components that were already in the relative composition matrix. As previously noted, the amount of each component of the gas sample is expressed as a percentage of the whole sample. Therefore, adding the Raman-invisible gas to the relative composition matrix requires the re-calculation of all the components which were already in the matrix.

Figure 3:
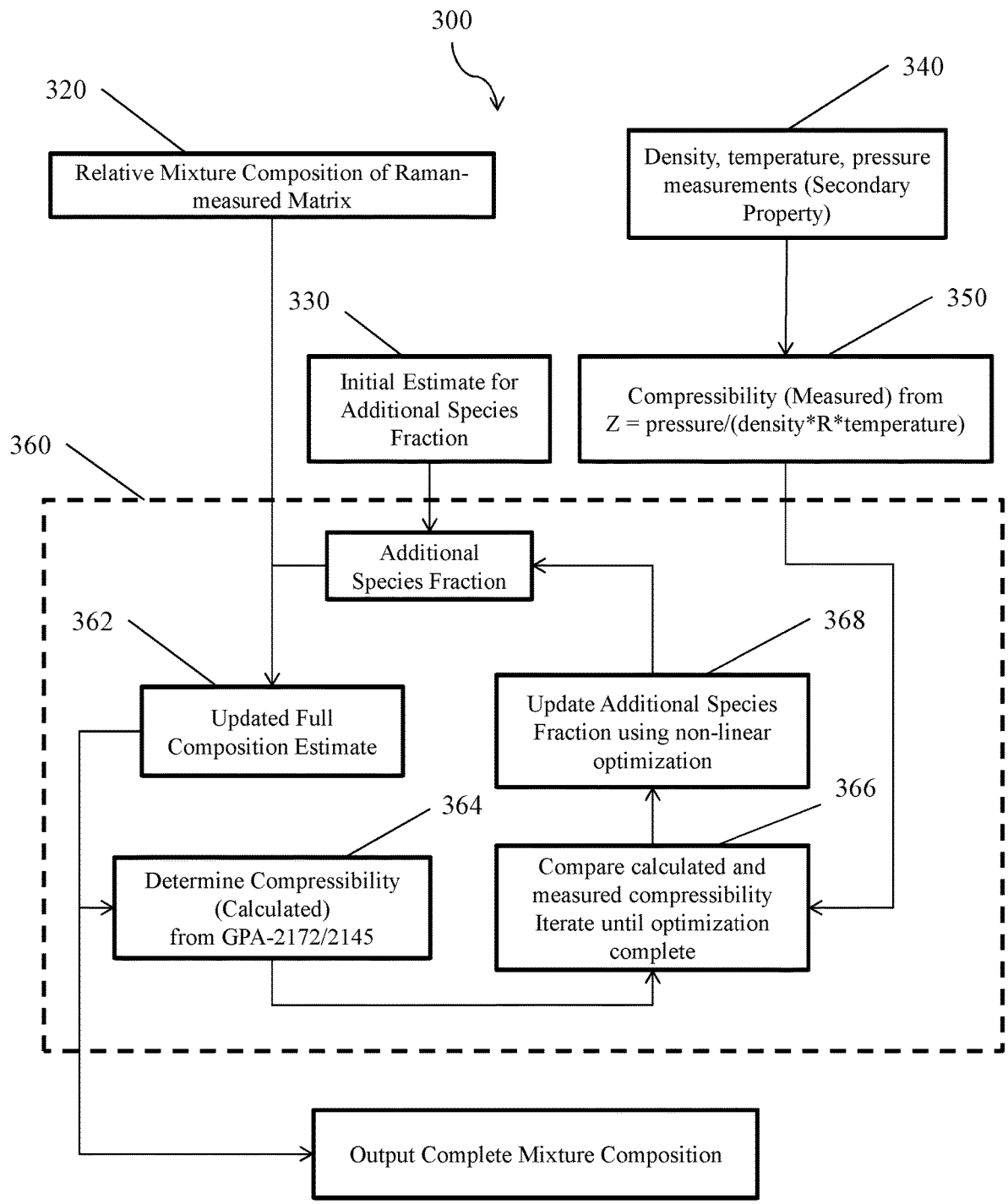
FIG. 3 shows an exemplary calculation of the mixture composition using a non-linear iterative method.

A method 300 according to at least one embodiment of the present disclosure is shown in FIG. 3. The method 300 may be performed on a multi-component gas sample contained in a sample chamber.

The method 300 includes a Raman spectroscopic analysis of the gas sample to generate and to capture a Raman spectrum of the gas sample, which is not shown in FIG. 3.

The method 300 includes a step 320 of calculating the relative composition of the gas sample from the Raman spectrum and producing a matrix of the components of the gas sample. The step 320 includes normalizing the components of the matrix by expressing each Raman-detected component as a ratio of the amount of that component to the sum of the amounts of all Raman-detected components. The result of step 320 is a relative composition matrix containing the amounts of each Raman-detected component in the gas sample.

The method 300 includes a step 330 of making an initial estimate of the molar amount of the Raman-invisible component. The initial estimate can be based on an expectation of the amount of the Raman-invisible component present, or the initial estimate can be based on prior analyses of similar gas mixtures. The value of the initial estimate is normalized; that is, it is expressed as a percent of the whole sample.

The method 300 includes a step 340 of measuring one or more secondary properties of the gas mixture. In the embodiment shown in FIG. 3, the density, pressure, and temperature of the gas sample are measured in step 340, but other secondary properties may be measured and used as well.

The method 300 includes a step 350 of calculating the compressibility factor of the gas mixture using the secondary properties measured in step 340.

The method 300 includes a step 360 of calculating the normalized molar value of the Raman-invisible component. Step 360 may be performed one or more times to calculate iteratively a final value for the Raman-invisible component. The first iteration of step 360 uses the initial estimate of the molar value of the Raman-invisible component from step 330. A subsequent iteration of step 360 uses the molar value of the Raman-invisible component calculated in the iteration of step 360 previous to that subsequent iteration.

The method step 360 includes a step 362 of re-calculating the relative composition matrix of the gas sample. In step 362 the molar value of the Raman-invisible gas is added to the relative composition matrix. Or if the molar value of the Raman-invisible gas is already in the matrix from a previous iteration of method step 360, that value is replaced with the new value described in the preceding paragraph. The molar fractions of the other components in the matrix are re-calculated to account for the added or new molar value of the Raman-invisible gas.

The method step 360 includes a step 364 of calculating the compressibility factor of the gas mixture using the complete composition matrix as an input.

The method step 360 includes a step 366 of comparing the value of the compressibility factor calculated in step 364 with the value of the compressibility factor calculated in step 350. If the difference between the two calculated values of the compressibility factor is less than a threshold, the iterations of step 360 are complete. The last estimated molar value of the Raman-invisible component is the final value.

However, if the difference calculated in step 366 is greater than the threshold, the method step 360 may include a step 368 of adjusting the estimated molar value of the Raman-invisible component to reduce the difference in the two calculated compressibility factors in the next iteration of method step 360. The method step 360 may be executed iteratively to reduce the difference between the two calculated compressibility factors to a value less than the threshold.

When the iterations of step 360 have been completed, i.e., when the difference between the two calculated values of the compressibility factor is less than the threshold, the complete mixture composition matrix as determined in step 362 of the last iteration of method step 360 is output as the mixture composition matrix.

While various embodiments of a method for analyzing the components of a gas mixture have been described in considerable detail herein, the embodiments are merely offered by way of non-limiting examples of the disclosure described herein. It will therefore be understood that various changes and modifications may be made, and equivalents may be substituted for elements and steps thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Such sequences may be varied and still remain within the scope of the present disclosure. Therefore, the particular order of the steps disclosed herein should not be construed as limitations of the present disclosure.

What is claimed is:

1. A method for analyzing the composition of a multi-component gas sample, comprising:
    determining a first composition of a multi-component gas sample using a spectroscopic device;
    calculating a relative composition matrix containing a normalized molar amount of each component of the multi-component gas sample, based on the first composition;
    calculating an average molar mass of the relative composition matrix using a molar mass and the normalized molar amount of each component of the relative composition matrix;
    measuring a temperature, a pressure, and a density of the gas sample and calculating an inverse compressibility factor of the gas sample therefrom;
    calculating a molar amount of a spectroscopic-invisible gas using the average molar mass, the inverse compressibility factor, and a molar mass of the spectroscopic-invisible gas;
    adding the molar amount of the spectroscopic-invisible gas to the relative composition matrix; and
    adjusting the normalized molar amount of each component in the relative composition matrix to account for the molar amount of the spectroscopic-invisible gas.

2. The method of claim 1, wherein the spectroscopic device is a Raman spectroscopic device and spectroscopic-invisible is defined as invisible to Raman spectroscopy.

3. The method of claim 1, wherein the spectroscopic device is a near infrared/infrared absorption spectroscopic device and spectroscopic-invisible is defined as invisible to near infrared/infrared absorption spectroscopy.

4. A method for analyzing the composition of a multi-component gas sample, comprising:
    determining a first composition of a multi-component gas sample using a spectroscopic device;
    calculating a relative composition matrix containing a normalized molar amount of each component of the multi-component gas sample, based on the first composition;
    measuring a temperature, a pressure, and a density of the gas sample and calculating a first compressibility factor of the gas sample therefrom;
    estimating a molar amount of a spectroscopic-invisible gas;
    adding the estimated molar amount of the spectroscopic-invisible gas to the relative composition matrix;
    adjusting the normalized molar amount of the other components in the relative composition matrix to account for the estimated molar amount of the spectroscopic-invisible gas;
    calculating a second compressibility factor of the gas sample using the relative composition matrix;
    determining whether a difference between the first compressibility factor and the second compressibility factor exceeds a threshold, wherein upon determining that the difference exceeds the threshold:
    adjusting the estimated molar amount of the spectroscopic-invisible gas in the relative composition matrix such that the difference between the first compressibility factor and the second compressibility factor is reduced;
    repeating the adjusting of the normalized molar amount of each component in the relative composition matrix, the calculating a second compressibility factor, and the determining whether a difference between the first compressibility factor and the second compressibility factor exceeds the threshold until the difference does not exceed the threshold.

5. The method of claim 4, wherein the spectroscopic device is a Raman spectroscopic device and spectroscopic-invisible is defined as invisible to Raman spectroscopy.

6. The method of claim 4, wherein the spectroscopic device is a near infrared/infrared absorption spectroscopic device and spectroscopic-invisible is defined as invisible to near infrared/infrared absorption spectroscopy.

* * * * *